United States Patent [19]

Wang et al.

[11] Patent Number: 5,827,187

[45] Date of Patent: Oct. 27, 1998

[54] DYNAMIC MR DIGITAL SUBTRACTION ANGIOGRAPHY WITH COMPLEX SUBTRACTION

[75] Inventors: Yi Wang; Richard L. Ehman, both of Rochester, Minn.

[73] Assignee: Mayo Foundation for Medical Education and Research, Rochester, Minn.

[21] Appl. No.: 739,534

[22] Filed: Oct. 30, 1996

Related U.S. Application Data

[60] Provisional application No. 60/016,063, Apr. 23, 1996.

[51] Int. Cl.$^6$ ................................................ A61B 5/055
[52] U.S. Cl. ......................... 600/419; 600/420; 324/306; 324/309
[58] Field of Search ............................ 128/653.2, 653.3, 128/653.4; 324/306, 309; 600/410, 419, 420

[56] References Cited

U.S. PATENT DOCUMENTS

| | | | |
|---|---|---|---|
| 5,109,854 | 5/1992 | Provost | 128/653.2 |
| 5,285,158 | 2/1994 | Mistretta et al. | 128/653.3 |
| 5,565,776 | 10/1996 | Kanazawa | 324/306 |

OTHER PUBLICATIONS

Dynamic MR Digital Subtraction Angiography Using Contrast Enhancement, Fast Data Acquisition, and Complex Subtraction, MRM 36:551–556 (1996), Wang, et al.

Gadolinium–enhanced MR Aortography, Radiology 1994; 191:155–164, M.R. Prince.

Dynamic Contrast–enhanced Subtraction MR Angiography of the Lower Extremities: Initial Evaluation with a Multi-section Two–dimensional Time–of–Flight Sequence, Radiology 1995; 196:689–695, Adamis, et al.

Fast MR Angiography of the Aortoiliac Arteries and Arteries of the Lower Extremity: Value of Bolus–Enhanced, Whole–Volume Subtraction Technique, AJR 1995; 165:431–437, Douek, et al.

Projection Angiograms of Blood Labeled by Adiabatic Fast Passage, MRM 3, 454–462 (1986) Dixon, et al.

Magnetic Resonance Angiography, Radiology 1986; 161:717–720, Dumoulin, et al.

MR Angiography by Selective Inversion Recovery, MRM 4, 193–202 (1987), Nishimura, et al.

Quantitive Velocity Images from Thick Slab 2D Phase Contrast, MRM 29:216–225 (1993), Weber, et al.

Generalized Matched Filtering for Time–Resolved MR Angiography of Pulsatile Flow, MRM 30:600–608 (1993), Wang, et al.

Carotid Artery: Prospective Blinded Comparison of Two–dimensional Time–of–Flight MR Angiography with Conventional Angiography and Duplex US, Radiology 1993; 186:339–344, Huston, et al.

Chapter 4, Applied Anatomy of the Heart, Part II Structure and Function, 75–76.

*Primary Examiner*—Ruth S. Smith
*Attorney, Agent, or Firm*—Quarles & Brady

[57] ABSTRACT

A dynamic MR angiography technique, MR digital subtraction angiography (MR DSA), based on fast acquisition, contrast enhancement and complex subtraction is described. When a bolus of contrast is injected into a patient, data acquisition begins, dynamically acquiring a thick slab using a fast gradient echo sequence for 1060 sec. Similar to x-ray DSA, a mask is selected from the images without contrast enhancement, and later images are subtracted from the mask to generate angiograms. Complex subtraction is used to overcome the partial volume effects related to the phase difference between the flowing and stationary magnetization in a voxel.

7 Claims, 5 Drawing Sheets

DYNAMIC MR DIGITAL SUBTRACTION ANGIOGRAPHY WITH COMPLEX SUBTRACTION

This application claims benefit of U.S.A. Provisional Appln. No. 60/016,063, filed Apr. 23, 1996.

BACKGROUND OF THE INVENTION

The field of the invention is magnetic resonance angiography ("MRA"), and particularly, dynamic studies of the human vasculature using contrast agents.

When a substance such as human tissue is subjected to a uniform magnetic field (polarizing field $B_0$), the individual magnetic moments of the spins in the tissue attempt to align with this polarizing field, but precess about it in random order at their characteristic Larmor frequency. If the substance, or tissue, is subjected to a magnetic field (excitation field $B_1$) which is in the x-y plane and which is near the Larmor frequency, the net aligned moment, $M_z$, may be rotated, or "tipped", into the x-y plane to produce a net transverse magnetic moment $M_t$.

A signal is emitted by the excited spins, and after the excitation signal $B_1$ is terminated, this signal may be received and processed to form an image.

When utilizing these signals to produce images, magnetic field gradients ($G_x$, $G_y$, and $G_z$) are employed.

Typically, the region to be imaged is scanned by a sequence of measurement cycles in which these gradients vary according to the particular localization method being used. The resulting set of received NMR signals are digitized and processed to reconstruct the image using one of many well known reconstruction techniques.

Conventional MR angiography (MRA) techniques are based on a natural flow contrast derived from time-of-flight (TOF) and phase-contrast (PC) effects. It is well known that this flow contrast is not simply determined by the flow rate. Other factors such as flow type, vessel orientation and velocity encoding gradients can significantly affect the flow contrast, causing problems such as in-plane flow saturation artifacts and over estimation of stenoses due to turbulence-caused signal loss. In addition, the natural flow contrast is typically small and a long scan time is required to obtain an adequate signal-to-noise ratio (SNR).

Recently it has been recognized that contrast agents can be employed to provide flow contrast for MR angiography. Both multi-slice 2D and 3D fast gradient echo techniques have been used in dynamic studies to acquire a volume data set with contrast agent infusion. Projection angiograms can be generated using maximum-intensity-projection (MIP) through this volume data (consisting of multiple sections). In order to avoid background enhancement, it is essential in these dynamic studies to capture the contrast agent in the arterial phase and complete the volume data acquisition before the venous phase. This requires accurate bolus timing, which is patient- and anatomy-dependent. This is accomplished by acquiring a series of images after injection of the contrast agent and selecting the image from this series which provides best the contrast.

Magnitude subtraction has been used to further enhance the image contrast by reducing the background signal produced by stationary tissues. The volume data set with bolus infusion of contrast agent is subtracted from a mask volume data set acquired before contrast infusion to produce a difference volume data set. Successful magnitude subtraction requires that the thickness of each section, or slice, of acquired data be less than the diameter of blood vessels, otherwise partial volume effects cause signal dropout artifacts. This phenomenon has precluded the use of thick-slice 2D acquisitions of NMR data for such digital subtraction angiography methods.

SUMMARY OF THE INVENTION

The present invention stems from the discovery that partial volume effects can be overcome using complex subtraction of two MR data sets. Thus, projection angiograms can be generated by complex subtracting the thick slab MR images acquired during contrast infusion from an MR mask image acquired without infused contrast agent. Fast 2D MRA data acquisition of a thick slab is used to dynamically monitor contrast bolus passage in the vascular system contained in the slab. Such thick slab acquisitions can be performed at a higher temporal rate than the usual 3D acquisitions, thus assuring that an MRA image data set will be acquired at the optimal moment in the dynamic study.

A general object of the invention is to improve the quality of MRA images acquired during dynamic studies. By complex subtracting two images acquired at different times in the dynamic study, background signal can be suppressed without producing partial volume effects. By complex subtracting two images, signal loss due to partial volume effects is avoided and thick slab acquisitions can be performed.

Another object of the invention is to increase the temporal rate at which NMR images are acquired during a dynamic study. Because a thick slab 2D acquisition can be employed, 2DFT pulse sequences can be employed rather than the more time consuming 3DFT pulse sequences. This enables more images to be acquired during the dynamic studies.

The foregoing and other objects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims herein for interpreting the scope of the invention.

DESCRIPTION OF THE PREFERRED EMBODIMENT

Figure 1:
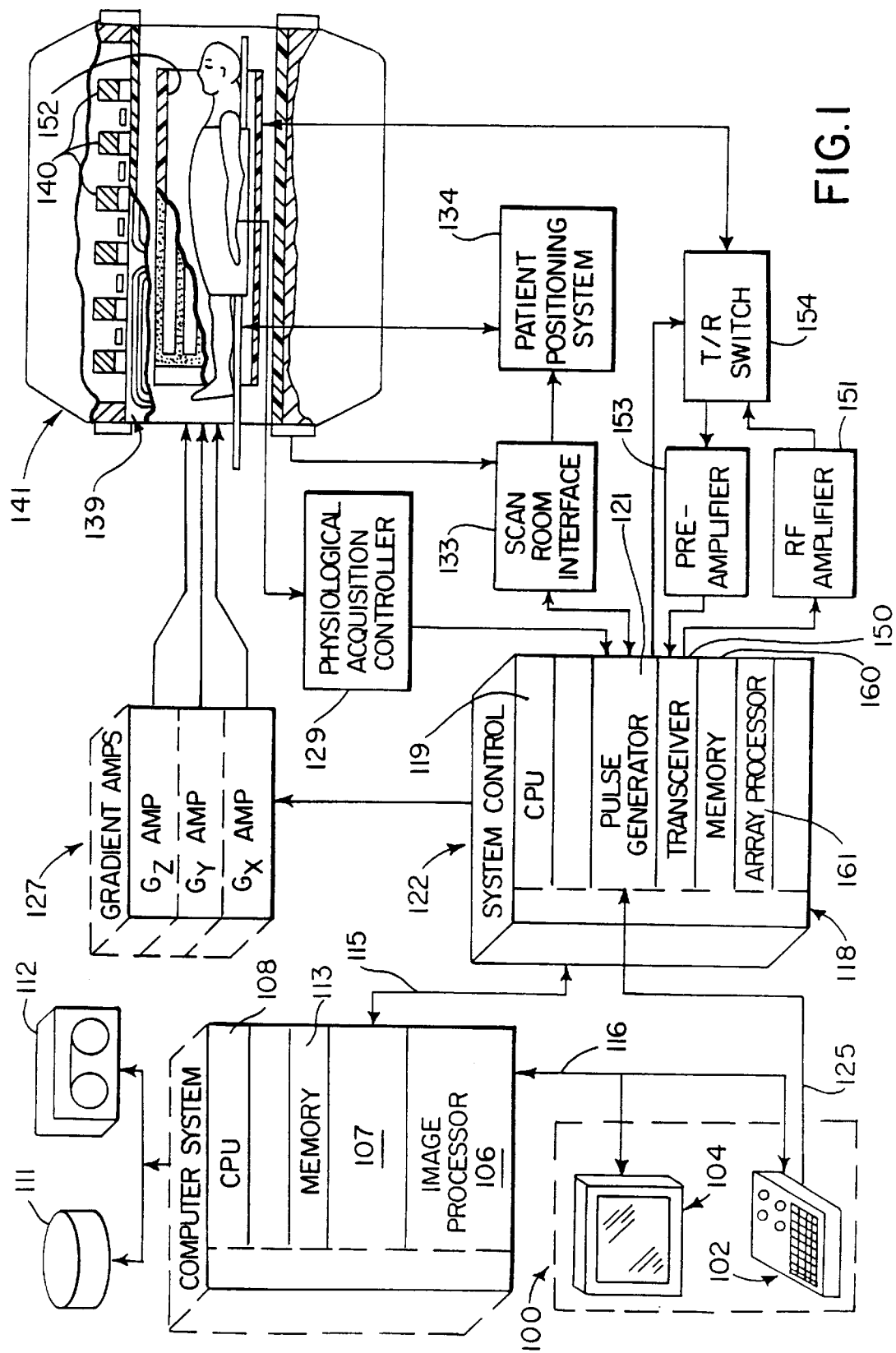
FIG. 1 is a block diagram of an MRI system which employs the present invention.

Referring first to FIG. 1, there is shown the major components of a preferred MRI system which incorporates the present invention. The operation of the system is controlled from an operator console 100 which includes a keyboard and control panel 102 and a display 104. The console 100 communicates through a link 116 with a separate computer system 107 that enables an operator to control the production and display of images on the screen 104. The computer system 107 includes a number of modules which communicate with each other through a backplane. These include an image processor module 106, a CPU module 108 and a memory module 113, known in the art as a frame buffer for storing image data arrays. The computer system 107 is linked to a disk storage 111 and a tape drive 112 for storage of image data and programs, and it communicates with a separate system control 122 through a high speed serial link 115.

The system control 122 includes a set of modules connected together by a backplane. These include a CPU module 119 and a pulse generator module 121 which connects to the operator console 100 through a serial link 125. It is through this link 125 that the system control 122 receives commands from the operator which indicate the scan sequence that is to be performed. The pulse generator module 121 operates the system components to carry out the desired scan sequence. It produces data which indicates the timing, strength and shape of the RF pulses which are to be produced, and the timing of and length of the data acquisition window. The pulse generator module 121 connects to a set of gradient amplifiers 127, to indicate the timing and shape of the gradient pulses to be produced during the scan. The pulse generator module 121 also receives patient data from a physiological acquisition controller 129 that receives signals from a number of different sensors connected to the patient, such as ECG signals from electrodes or respiratory signals from a bellows. And finally, the pulse generator module 121 connects to a scan room interface circuit 133 which receives signals from various sensors associated with the condition of the patient and the magnet system. It is also through the scan room interface circuit 133 that a patient positioning system 134 receives commands to move the patient to the desired position for the scan.

The gradient waveforms produced by the pulse generator module 121 are applied to a gradient amplifier system 127 comprised of $G_x$, $G_y$ and $G_z$ amplifiers. Each gradient amplifier excites a corresponding gradient coil in an assembly generally designated 139 to produce the magnetic field gradients used for position encoding acquired signals. The gradient coil assembly 139 forms part of a magnet assembly 141 which includes a polarizing magnet 140 and a whole-body RF coil 152. A transceiver module 150 in the system control 122 produces pulses which are amplified by an RF amplifier 151 and coupled to the RF coil 152 by a transmit/receive switch 154. The resulting signals radiated by the excited nuclei in the patient may be sensed by the same RF coil 152 and coupled through the transmit/receive switch 154 to a preamplifier 153. The amplified NMR signals are demodulated, filtered, and digitized in the receiver section of the transceiver 150. The transmit/receive switch 154 is controlled by a signal from the pulse generator module 121 to electrically connect the RF amplifier 151 to the coil 152 during the transmit mode and to connect the preamplifier 153 during the receive mode. The transmit/receive switch 154 also enables a separate RF coil (for example, a head coil or surface coil) to be used in either the transmit or receive mode.

The NMR signals picked up by the RF coil 152 are digitized by the transceiver module 150 and transferred to a memory module 160 in the system control 122. When the scan is completed and an entire array of data has been acquired in the memory module 160, an array processor 161 operates to Fourier transform the data into an array of image data. This image data is conveyed through the serial link 115 to the computer system 107 where it is stored in the disk memory 111. In response to commands received from the operator console 100, this image data may be archived on the tape drive 112, or it may be further processed by the image processor 106 and conveyed to the operator console 100 and presented on the display 104.

Figure 2:
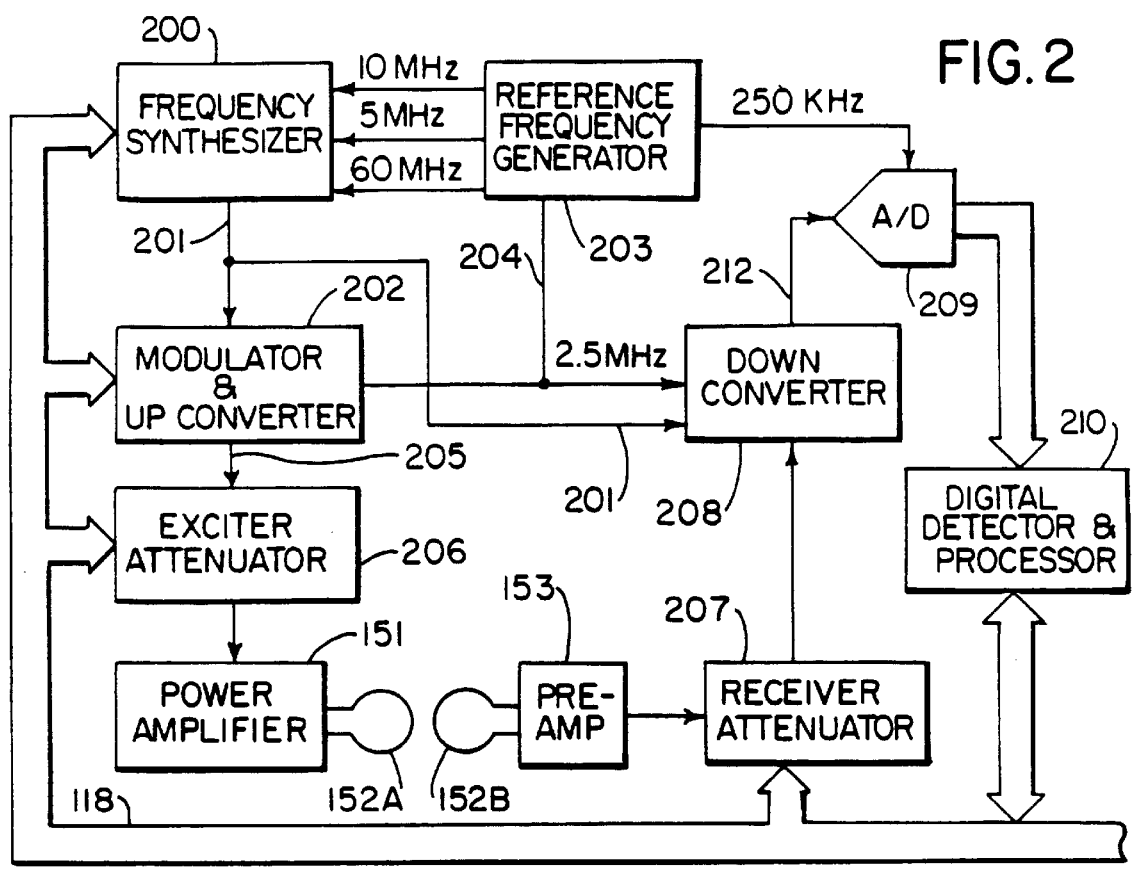
FIG. 2 is an electrical block diagram of the transceiver which forms part of the MRI system of FIG. 1.

Referring particularly to FIGS. 1 and 2, the transceiver 150 produces the RF excitation field B1 through power amplifier 151 at a coil 152A and receives the resulting signal induced in a coil 152B. As indicated above, the coils 152A and B may be separate as shown in FIG. 2, or they may be a single wholebody coil as shown in FIG. 1. The base, or carrier, frequency of the RF excitation field is produced under control of a frequency synthesizer 200 which receives a set of digital signals (CF) from the CPU module 119 and pulse generator module 121. These digital signals indicate the frequency and phase of the RF carrier signal produced at an output 201. The commanded RF carrier is applied to a modulator and up converter 202 where its amplitude is modulated in response to a signal R(t) also received from the pulse generator module 121. The signal R(t) defines the envelope of the RF excitation pulse to be produced and is produced in the module 121 by sequentially reading out a series of stored digital values. These stored digital values may, in turn, be changed from the operator console 100 to enable any desired RF pulse envelope to be produced.

The magnitude of the RF excitation pulse produced at output 205 is attenuated by an exciter attenuator circuit 206 which receives a digital command, TA, from the backplane 118. The attenuated RF excitation pulses are applied to the power amplifier 151 that drives the RF coil 152A. For a more detailed description of this portion of the transceiver 122, reference is made to U.S. Pat. No. 4,952,877 which is incorporated herein by reference.

Referring still to FIG. 1 and 2 the signal produced by the subject is picked up by the receiver coil 152B and applied through the preamplifier 153 to the input of a receiver attenuator 207. The receiver attenuator 207 further amplifies the signal by an amount determined by a digital attenuation signal (RA) received from the backplane 118.

The received signal is at or around the Larmor frequency, and this high frequency signal is down converted in a two step process by a down converter 208 which first mixes the NMR signal with the carrier signal on line 201 and then mixes the resulting difference signal with the 2.5 MHz reference signal on line 204. The down converted NMR signal is applied to the input of an analog-to-digital (A/D) converter 209 which samples and digitizes the analog signal and applies it to a digital detector and signal processor 210 which produces 16-bit in-phase (I) values and 16-bit quadrature (Q) values corresponding to the received signal. The resulting stream of digitized I and Q values of the received signal are output through backplane 118 to the memory module 160 where they are employed to reconstruct an image.

The 2.5 MHz reference signal as well as the 250 kHz sampling signal and the 5, 10 and 60 MHz reference signals are produced by a reference frequency generator 203 from a common 20 MHz master clock signal. For a more detailed description of the receiver, reference is made to U.S. Pat. No. 4,992,736 which is incorporated herein by reference.

Data acquisition begins when a bolus contrast agent (Gadoteridol, 0.1 mmol/kg, greater than 1 ml/sec. injection rate) is injected into the patient's median cubital vein and continues for 10 to 100 sec. A fast gradient echo sequence with a through-plane dephaser option was implemented on a standard 1.5T MR imager (Signa, General Electric Company, Milwaukee) to acquire a thick slab (thickness 40–160 mm and FOV along the frequency direction $FOV_f$ = 200–480 mm to cover the anatomy of interest). Imaging parameters were $N_x$=256, $N_y$=128, 160, 192 or 256 (corresponding to approximately 1.3–2.6 sec/image), square pixel when desired, TE/TR=2.5–3.1/9.9–11.0 (depending on pixel size), flip angle 45°. A multiple receiver coil array appropriate for the anatomy under study is used whenever possible. To suppress motion artifacts, patients are instructed to hold their breath as long as they can in body applications.

Figure 3:
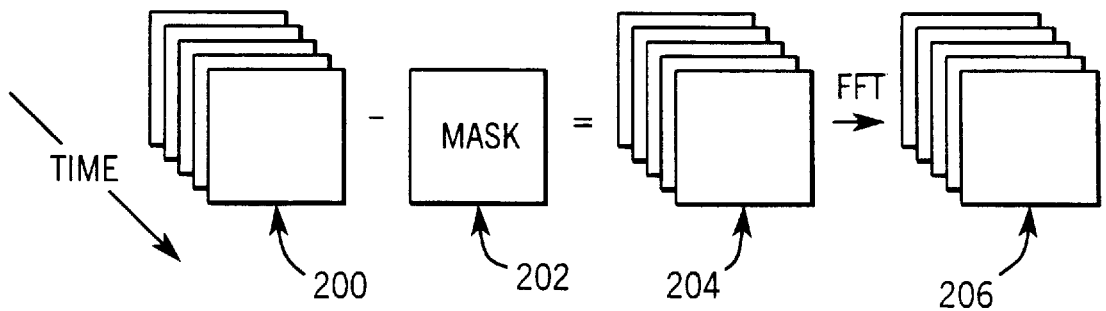
FIG. 3 is a pictorial representation of the data structures produced by the preferred embodiment of the invention.
Figure 6:
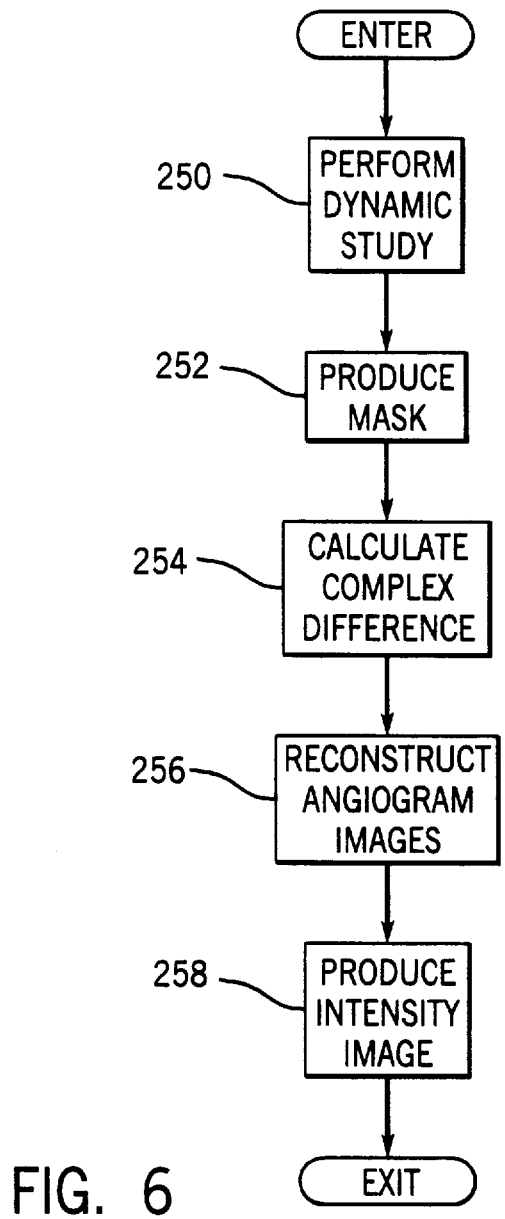
FIG. 6 is a flow chart of the steps performed by the MRI system of FIG. 1 to practice the present invention.

The preferred embodiment of the present invention is performed on the MRI system of FIG. 1 using programmed steps indicated in FIG. 6. As shown by process block 250, the MRI system is directed to perform a dynamic study to acquire a series of complex k-space data sets 200 (eg. thirty) as shown in FIG. 3. The data sets 200 depict the subject at consecutive time frames during the dynamic study. At process block 252 a complex mask data set 202 is then produced using data acquired during the dynamic study. This mask 202 is chosen to depict the subject before contrast enhancement and is typically derived from the second time frame data set 200.

However, it is also possible to select as the k-space mask image 202 another one of the k-space temporal images 200. For example, the patient might move during the early part of the dynamic study, making the early temporal images 200 unsatisfactory. In this case the angiogram images 206 may not have as much contrast, but the vasculature is depicted more clearly.

Other methods for producing the mask 202, such as those used in x-ray digital subtraction angiography ("DSA") may also be used. For example, frequency-band limited complex temporal filters based on varying masks, similar to recursive filters, may be employed due to their relative insensitivity to patient motion. The signal to noise ratio of the final angiogram image may also be improved by combining angiogram frame images 206 using algorithms such as matched filters.

Referring to FIGS. 3 and 6, the next step as indicated at process block 254 is to calculate the complex difference between each time frame k-space data set 200 and the mask 202 to form corresponding complex difference k-space data sets 204. This step is performed by subtracting the $I_{202}$ and $Q_{202}$ values in the mask 202 from corresponding $I_{200}$ and $Q_{200}$ values in each k-space data set 200:

Complex Difference=$I_{200}$-$I_{202}$+$Q_{200}$-$Q_m$=$I_{204}$+$Q_{204}$

Each resulting 2D array of complex difference data 204 is then used to produce a corresponding angiogram image 206 by performing a two-dimensional Fast Fourier transform (FFT) as indicated at process block 256. The magnitude image is then calculated for each complex value in the angiogram images 206:

$$M = \sqrt{I_{206}^2 + Q_{206}^2}.$$

From this magnitude image an intensity image for the display 104 is produced as indicated at process block 258.

Figure 4:
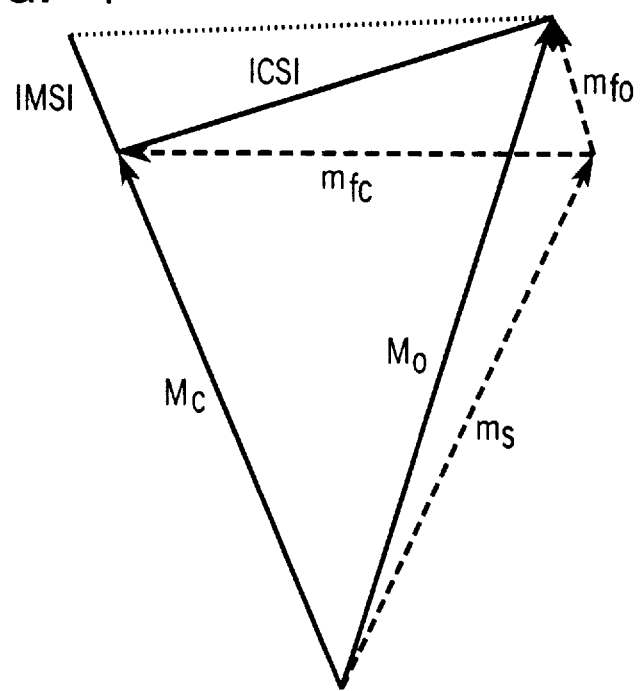
FIG. 4 is a vector diagram illustrating the complex subtraction step of the present invention.

The effect of a complex subtraction of the mask 202 from a temporal image 200 is illustrated in FIG. 4. The magnetization in a voxel (M) can be compartmentalized into a stationary component ($m_s$) and a flowing component ($m_f$). Using the notation that subscript "0" represents no contrast and subscript "c" represents contrast, the complex subtraction can be expressed as:

$$M_c = M_0 = (m_s + m_{fc}) - (m_s + m_{f0}) = m_{fc} - m_{f0} \approx m_{fc} \qquad (1)$$

Hence, the magnitude of the complex subtraction ("CS" in FIG. 4) yields an angiogram, with values proportional to the enhancement of blood signal. For multiple receiver coils, the complex subtraction and FFT are performed for the data acquired from each individual coil and an angiogram is generated by summing the real space image magnitudes from all coils. Angiograms at sequential times can also be selectively combined using a matched filter to generate an angiogram of higher SNR.

The reason why simple magnitude subtraction is not appropriate is also illustrated in FIG. 4. By definition, magnitude subtraction is performed on magnitude images in image space, as it is the case in x-ray DSA. In general, magnitude subtraction $$|M_c| - |M_0| = \sqrt{|m_s|^2 + 2m_s \cdot m_{fc} + |m_{fc}|^2} - \sqrt{|m_s|^2 + 2m_s \cdot m_{f0} + |m_{f0}|^2} \qquad (2)$$

depends on partial volume effects, that is, it depends on the fraction of flow magnetization in the voxel and the angulation between the stationary spins and the flowing spins.

A thick slab is used in the preferred embodiment to cover the anatomy of interest and a voxel in such a slab may contain both flowing and stationary spins (partial volume effects). The basic phenomenon that causes simple magnitude subtraction to fail is that the magnetization of the flowing blood and the stationary magnetization are not in phase. In the presence of partial volume effects, therefore, intravascular contrast can either increase or decrease the net signal in a voxel, though it always enhances the flow magnetization. A substantial error will thus occur in angiograms generated by magnitude subtraction. It is a discovery of the present invention that complex subtraction will eliminate such error caused by partial volume effects.

Figure 5A:
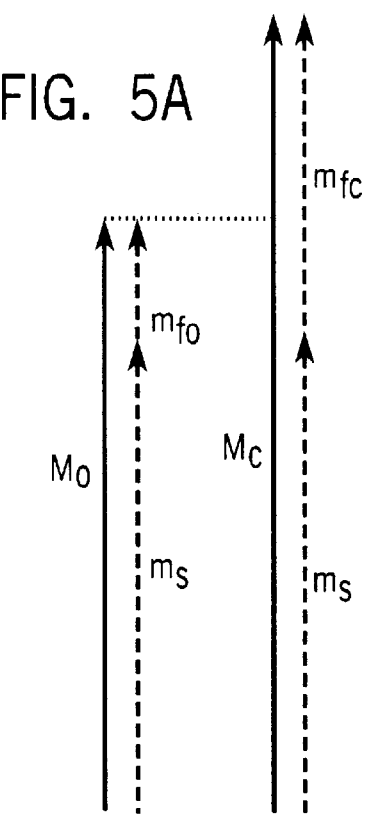
FIGS. 5a–c are vector diagrams illustrating three different magnetization situations encountered in MRA applications.
Figure 5B:
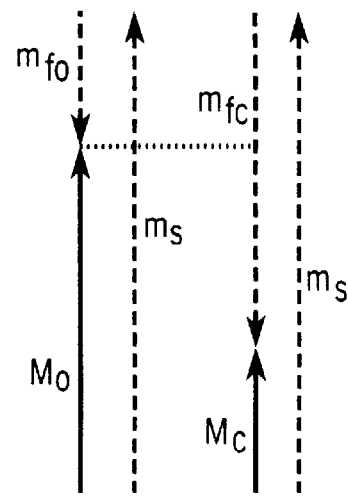
Figure 5C:
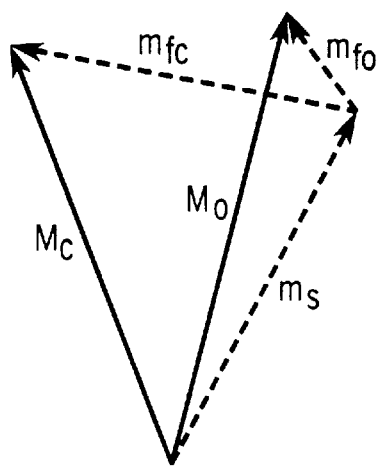

This is illustrated by the three examples in FIGS. 5a–c. FIG. 5a depicts the simplest situation when all the magnetization vectors (stationary $m_s$, flow without contrast $m_{f0}$, flow with contrast $m_{fc}$) are in the same direction. In this case, contrast agent infusion will increase total signal ($|M_c|>|M_0|$), and magnitude subtraction provides a result similar to complex subtraction.

In FIG. 5b, both flow magnetization vectors ($m_{f0}$, $m_{fc}$) are in opposite direction to the stationary one ($m_s$). Though the contrast agent increases the magnitude of flow magnetization ($|m_{fc}|>|m_{f0}|$), it reduces the magnitude of the total magnetization in a voxel ($|M_c|<|M_0|$). In this case, black enhancement will be observed in the temporal magnitude images and the magnitude subtraction provides the opposite result of the complex subtraction method.

In FIG. 5c, contrast agent changes not only the magnitude but also the phase of flow magnetization. However, the magnitude of the total magnetization in a voxel remains the same ($|M_c|=|M_0|$). In this case, no enhancement will be observed in the temporal magnitude images, since the magnitude subtraction yields a null value. However, in this case the complex subtraction method yields a value close to the enhancement of flow magnetization ($\approx m_{fc}$).

An advantage of the invention is that it improves the temporal resolution of the dynamic study. The temporal resolution of MR DSA is related to the desired spatial resolution and the performance of the gradient hardware. The present invention enables the acquisition of a thick slab, and this uses a small slice selection gradient, resulting in a shorter echo time and shorter repetition time. On a standard 1.5 T system, adequate angiograms can be generated as fast as 1.3 sec per image, at TE/TR=2.5/10 msec and 128 phase encodes. The use of faster gradient hardware currently available can reduce TE/TR to as short as 1/5 msec. This reduces acquisition time to the range of 0.6 sec at the same 256×128 acquisition matrix. The use of a very short TE (~1 msec) significantly reduces the dephasing loss due to turbulence at stenosis sites and possible destructive interference of crossing vessels.

Spatial resolution of MR DSA is characterized by both the pixel size (in-plane resolution) and the number of viewing angles (through resolution). The pixel size must be small enough to resolve the vessels of interest. Rotation at two or more projection angles may be required to resolve crossing vessel interference, a limitation shared by conventional x-ray angiography. The spatial resolution used in MR DSA should be application specific. For example, more than one projection view is likely to be necessary for intracranial MRA, but a single projection angle may be sufficient for evaluating the run-off arteries in the leg.

While the present invention makes it unnecessary to employ a 3D data acquisition, nevertheless, the present invention may also be employed to improve the quality of MR DSA images produced from a 3D data acquisition. Section thickness in such fast 3D acquisitions is typically several millimeters, and the partial volume effects that exist for vessels with a diameter of about 1 mm or less can be eliminated by using the complex difference method of the present invention.

The use of the present invention in a 3D acquisition has been demonstrated using a 3D gradient echo pulse sequence ("3 dfgre") implemented on the MRI system of FIG. 1 equipped with a fast gradient system. This 3D pulse sequence has a TE of 1.2 ms. and a TR of 5.1 ms. A flip angle of 30 degrees is employed in this pulse sequence and 16 separate phase encodings ($N_z$=16) are performed along the z axis and 128 separate phase encodings ($N_y$=128) are performed along the y axis. Each NMR signal is sampled 256 times ($N_x$256).

Three 3D temporal data sets are acquired within a 33 second breath-hold and two additional 3D data sets are created by view sharing between the three acquired 3D data sets. As with the 2D implementation, one of the five 3D data sets is chosen as a mask and the complex difference between the values therein and the corresponding values in another one of the 3D data sets is calculated as described above. The resulting complex difference 3D data set is then used to produce a 3D image by performing a 3D Fourier transformation along the three dimensions thereof.

Thus, for better depiction of small vessels in either 2D MR DSA or 3D MR DSA, the complex difference method of the present invention should be used.

Signal-to-noise ratio (SNR) is related to both spatial and temporal resolution. Contrast dose is another very important factor that determines SNR. At a dose of 0.1 mmol/kg of contrast material (single dose), the T1 relaxation time of arterial blood T1 is shortened to less than 100 msec, corresponding to a 4.5 times SNR enhancement at a sequence repetition time 10 msec. We found that this single dose can provide very high SNR. A lower contrast dose may provide sufficient SNR, and allow multiple small doses to be used to acquire different regions or projection angles.

Variations can be made from the preferred embodiment described above without departing from the spirit of the invention. For example, the acquired k-space data sets can be Fourier transformed before the complex subtraction with the mask data set. The results are the same, but a larger computational burden may be imposed if the mask data set must also be Fourier transformed.

It is claimed:

1. A method for producing an image of a patient with an MRI system, the steps comprising:

a) injecting a contrast agent into the patient b) acquiring complex NMR data using the MRI system to form a plurality of temporal data sets depicting the patient over a period of time during which the contrast agent affects the NMR data being acquired, each temporal data set containing a plurality of complex values;

c) producing a mask data set containing a plurality of complex values derived from the acquired temporal data sets;

d) producing a complex difference data set by calculating the complex difference between the complex values in the mask data set and the corresponding complex values in one of the temporal data sets; and e) producing an angiogram image from the complex difference data set.

2. The method as recited in claim 1 in which the angiogram image is produced by performing a Fourier transformation on the complex difference data set.

3. The method as recited in claim 2 in which the angiogram image is displayed by calculating the magnitude of complex values in the angiogram image.

4. The method as recited in claim 1 in which step b) is performed using a two-dimensional pulse sequence.

5. The method as recited in claim 1 in which step e) is accomplished by performing a two-dimensional Fourier transformation on the complex difference data set.

6. The method as recited in claim 1 in which step b) is performed using a three-dimensional pulse sequence.

7. The method as recited in claim 1 in which step e) is accomplished by performing a three-dimensional Fourier transformation on the complex difference data set.

* * * * *